United States Patent [19]

Whitehead

[11] Patent Number: 4,665,903
[45] Date of Patent: May 19, 1987

[54] PENILE PROSTHETIC DEVICE

[76] Inventor: Edgar D. Whitehead, 785 Park Ave., New York, N.Y. 10021

[21] Appl. No.: 774,442

[22] Filed: Sep. 10, 1985

Related U.S. Application Data

[63] Continuation of Ser. No. 520,058, Aug. 3, 1985, abandoned, which is a continuation-in-part of Ser. No. 336,166, Dec. 31, 1981, Pat. No. 4,399,812.

[51] Int. Cl.$^4$ ................................................ A61F 5/00
[52] U.S. Cl. ........................................ 128/79; 623/12
[58] Field of Search ...................... 128/79; 623/11, 12

[56] References Cited

U.S. PATENT DOCUMENTS 4,009,711  3/1977  Uson ...................................... 128/79
4,267,829  5/1981  Burton et al. .......................... 128/79
4,360,010  11/1982  Finney .................................. 128/79

Primary Examiner—Stephen C. Pellegrino
Attorney, Agent, or Firm—Charles E. Baxley

[57] ABSTRACT

Typical embodiments of the invention overcome male sexual dysfunction or impotence. Illustratively, a prosthetic device for implantation within the penis has a pumping mechanism that is integral with and is in fluid communication with two fluid storage sections. Fluid is pumped manually from the proximal storage section to distal storage section and then to four distal expansile sections that inflate to render the penis rigid and capable of sexual activity. Undesirable shrinkage of the erect penis is avoided through a rigid frame and bellows that prevent the proximal reservoir from contracting longitudinally and radially as fluid is withdrawn from this storage section to produce the erect penis.

4 Claims, 6 Drawing Figures

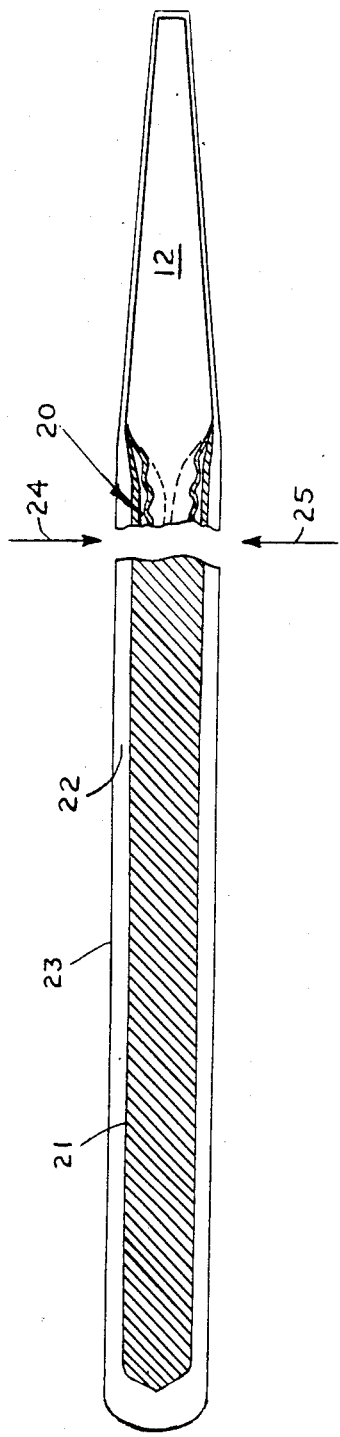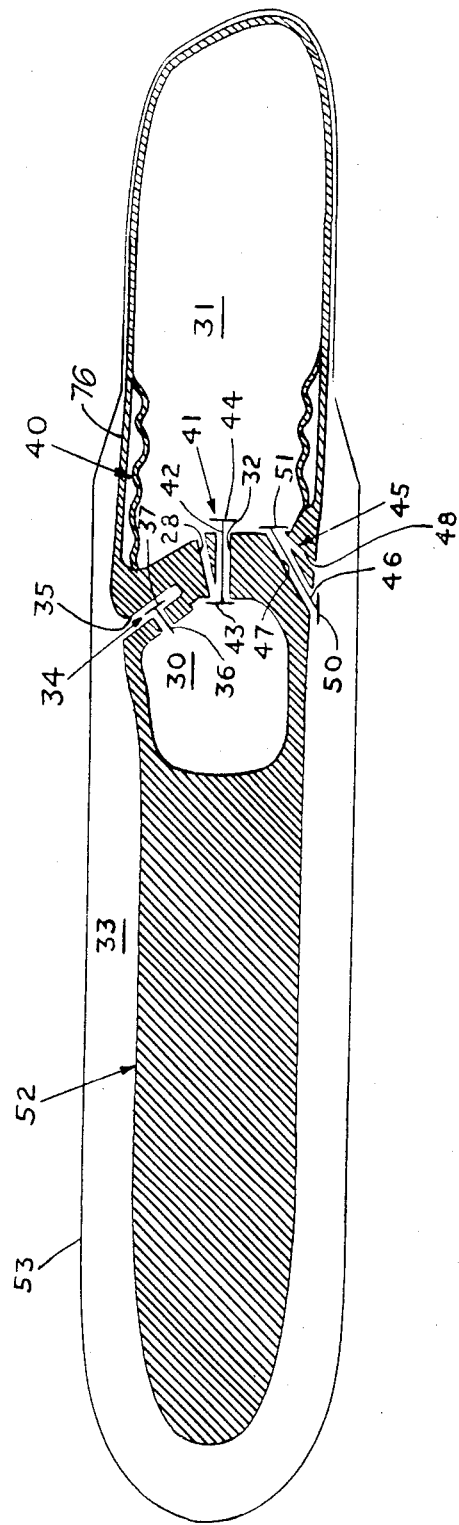

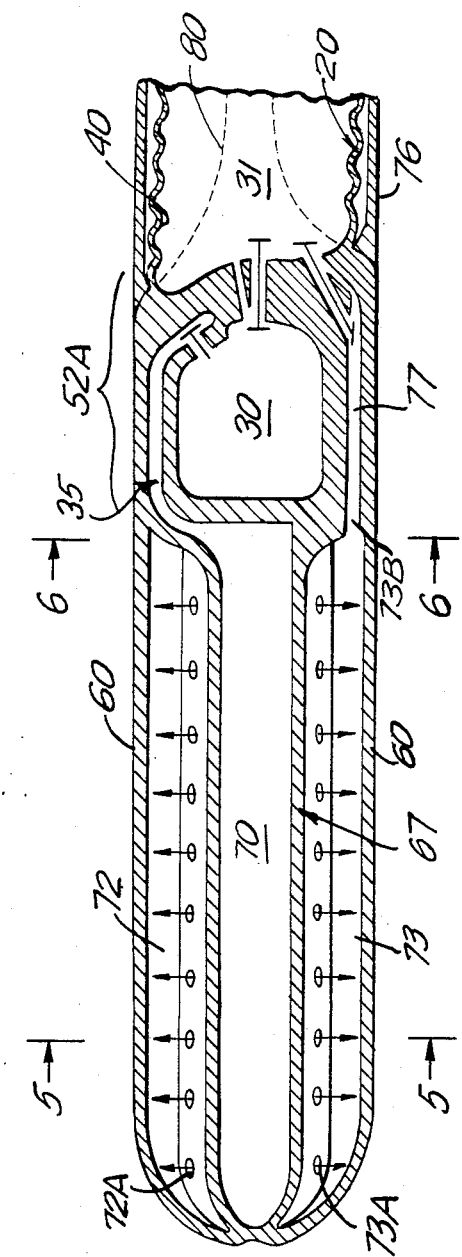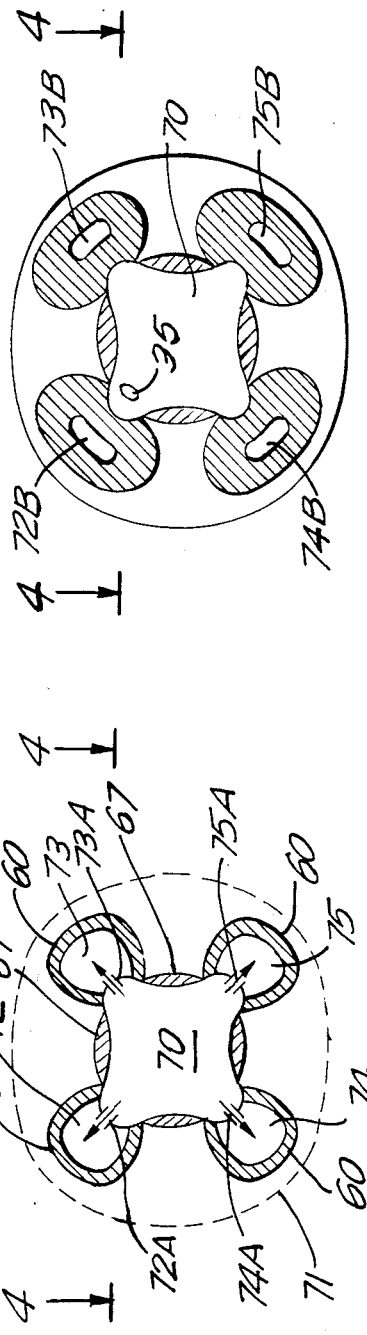

PENILE PROSTHETIC DEVICE

This is a continuation of application Ser. No. 520,058, filed Aug. 3, 1985 and now abandoned, which was a continuation-in-part of prior application Ser. No. 336,166 filed Dec. 31, 1981, now U.S. Pat. No. 4,399,812 granted Aug. 23, 1983.

This invention relates to prosthetic apparatus and, more specifically, to a prosthetic device for implantation within a penis in which a quantity of fluid is shifted within the device to produce selectively erect and flaccid penis conditions.

A number of prosthetic devices have been proposed for implantation within a penis, but each of these devices has limitations. Illustratively, the Small-Carrion prosthesis, the Finney prosthesis and the Jonas prosthesis require implantation of a pair of rods within the body of the penis. The Small-Carrion rods are quite rigid, often requiring use of restrictive clothing because of the permanent state of erection that is produced. The Finney and Jonas devices, however, do permit flexibility that enables the penis to be "dressed", that is, to assume a dependent position. All of these prosthetic devices nevertheless fail to increase the girth or turgor of the penis. The prosthetic devices themselves also might create a degree of urethral resistance that prevents subsequent endoscopic urologic investigation or treatment. The Finney and Jonas prostheses moreover have been known to buckle during coition.

The Scott prosthesis enables the penis to change from a flaccid state to a rigid state through a system that transfers hydraulic fluid from a reservoir in the abdomen to inflatable cylinders within the penis. Thus the Scott prosthesis imparts to the penis a normal selectively flaccid or erect appearance (including, during erection, normal increases in girth and in length). Although the Scott prosthesis overcomes a number of undesirable features of the Small-Carrion, Finney and Jonas devices, it is nevertheless unsatisfactory for several reasons. The Scott prosthesis is mechanically complicated and involves several components including inflatable penile cylinders, a scrotally located pumping device, an abdominally located fluid reservoir and associated tubing and connectors. Consequently the Scott apparatus is subject to mechanical failure and must be implanted through a relatively long and exacting surgical procedure.

In these circumstances there is a need for a selectively inflatable prosthesis that is mechanically simple and reliable and that also involves a relatively straightforward implantation surgical procedure which does not require special surgical instruments or skills, lengthy periods of hospitalization or great expense to the patient.

These objectives are attained through the practice of the present invention. Illustratively, within a unitary prosthetic device, two fluid storage sections are in fluid communication through a finger pressure operated pumping mechanism with four distal expansile sections. This prosthesis can be either a parallel double type, in which two independent and complete fluid transfer units are provided, one in each of two parallel devices, to, for example, deal with congential or acquired asymmetry of the corpora cavernosa; or a single conjoined type, for normal symmetrical corpora cavernosa, with one pumping mechanism and two fluid storage sections and four distal expansile sections.

In the parallel double prosthesis, the individual devices each are inserted through small respective incisions in the fibrous covering of the penis or tunica albuginea. In this way each device is implanted in one of the two bodies of erectile tissue or corpus cavernosa that lie side-by-side to form the larger protruberant part of the penis.

The single conjoined prosthesis, however, is placed in both corpora cavernosa through an incision in the tunica albuginea and by means of a division of the membrane partition that separates the two corpora cavernosa, the intercrural septum. The two diverging tails of this single conjoined prosthesis are placed in separate portions of the posterior part under the pubic arch, which is technically referred to as the ischial cavernosa or crura.

In either prosthetic device, the penis is made rigid through a sequence of manual compressions of the pumping mechanism. This manipulation draws fluid from one or more of the storage sections and transfers this fluid to the four distal expansion sections in order to inflate the expansile sections and thereby increase the girth, length and rigidity of the penis.

Because the parallel double prosthesis has two separate devices, each equipped with its own pumping mechanism, manipulation of only one pump provides for differential inflation of the penis on only one side of the intercrural septum. Should it be desired to inflate the other side of the penis, it will be necessary with the parallel double prosthesis, to manipulate the pumping mechanism in the other device.

To prevent over distension of the penis through pumping the fluid to too high a pressure as the penis is made rigid, a valve between the proximal fluid storage section and the distal expansile sections permits the fluid to flow back into the storage section, if the fluid pressure in the distal expansile section reaches a predetermined level.

There are a number of further technical problems, however, that are associated with devices of this character. Ordinarily, there is a relatively large volume of fluid that must be transferred between the proximal reservoir, or storage section, and the volume needed in the expansile sections. There also is a certain amount of reservoir shrinkage that occurs during those times in which fluid is being transferred from the reservoir to the balance of the device to establish a rigid erection. This reduction in storage volume has a self defeating result in that it tends to reduce the length of the erection. How, then, can the need for a large volume of pressurizing fluid be reconciled with the inherent shrinkage of the prosthetic device as fluid is being drawn from the reservoir to produce a satisfactorily erect and tumescent penis?

To cope with these problems, a semi-rigid distal reservoir will provide added fluid volume and forms one of two storage sections for the fluid.

A rigid cylinder around the bellows not only prevents the bellows from reducing the length of the erection, but also has the further benefit of preventing buckling and deflection during penile thrusting. This structure, moreover, can be incorporated in either a conjoint or double parallel prosthesis.

The invention will be appreciated more completely through a study of the following detailed description of preferred embodiments of the invention. The scope of the invention, however, is limited only through the claims appended hereto.

FIG. 1 is a plan view in full section of one embodiment of a device for a typical parallel double prosthesis that illustrates principles of the invention;

FIG. 3 is a side elevation in full section of the prosthesis shown in FIG. 2, taken along the line A—A of FIG. 2 and viewed in the direction of the arrows;

FIG. 4 is a longitudinal sectional view of a part of a device that incorporates additional features of the invention;

FIG. 5 is a transverse sectional view taken on line 5—5 of FIG. 4; and

Fig. 6 is transverse sectional view taken on line 6—6 of FIG. 4 of the invention shown in FIG. 4.

Figure 2:
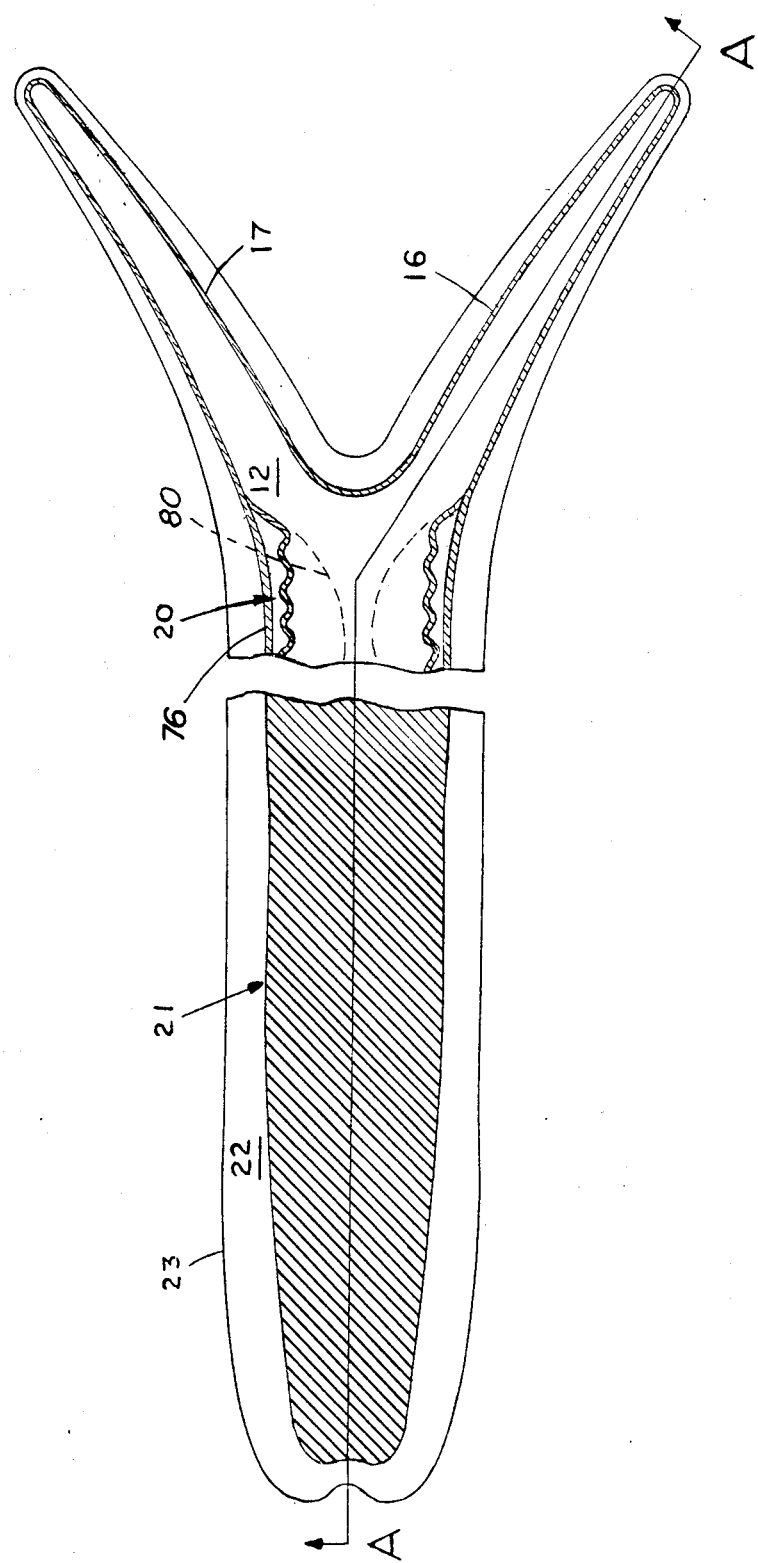
FIG. 2 is a plan view in full section of a typical conjoined single prosthesis illustrating principles of the invention.

The prosthesis shown in FIG. 1 is made of suitably flexible material to which the human body is tolerant, of which one or more of the silicone elastomers are typical.

Attention is invited to FIG. 1 which shows one of the two devices required for the parallel double prosthesis embodiment of the invention. As illustrated, an individual pumping mechanism 30 is in fluid communication with a pressurized fluid storage section 31 by way of a conduit 32. Fluid communication is selectively established with a distal expansile section 33 through a biased, or spring loaded check valve 34 and a passageway 35. The check valve 34 comprises a valve stem 36 that is received for longitudinal sliding movement within the fluid duct that joins the interior volume of the pumping mechanism 30 with the passageway 35. A valve seat 37 is connected to the end of the valve stem 36 that protrudes into the passageway 35.

In these circumstances, when the check valve 34 is closed to block fluid communication between the pumping mechanism 30 and the passageway 35, the valve seat 37 is pressed against the side of the passageway 35 in which the check valve 34 is mounted. With the check valve 34 open, however, the valve seat abuts the opposite side of the passageway 35. In this manner, the walls of the passageway 35 limit the movement of the valve seat 37 and retain the valve stem 36 within the fluid duct.

The fluid storage section 31 is an elongated, fluid filled bladder that is connected to the wall of the passageway 35 opposite to the pumping mechanism 30 and to a portion of the housing for the pumping mechanism by means of a bellows 40.

Fluid communication also is established from the fluid storage section 31 to the interior of the pumping mechanism 30 by way of a one-way check valve 41 in the conduit 32 and an angularly disposed side channel 28. As shown, the check valve 41 has a valve stem 42 that is somewhat longer than the conduit 32. Within the interior of the pumping mechanism 30 the valve stem 42 terminates in a valve seat 43 that, when pressed against the orifice of the conduits 28 and 32, blocks these passageways and prevents fluid from flowing from the pumping mechanism to the fluid storage section. Within the fluid storage section 31, that protruding portion of the valve stem 41 terminates in a transversely disposed stop 44, the diameter of the stop being appreciably greater than the diameter of the inlet to the conduit 32 but less than the inlet to the conduit 28. Thus, when the check valve 41 is open to permit fluid to flow into the pumping mechanism from the storage section 31, the stop nevertheless retains the valve stem 42 within the conduit 32 but enables fluid to flow from the reservoir 31 into the pumping mechanism 30 by way of the angularly disposed channel 28.

The fluid storage section 31 also is equipped with a biased, or spring loaded pressure relief valve 45 that permits fluid to flow from the distal expansile section 33 back into the fluid storage section if the pressure in the expansile section becomes higher than some predetermined limit of safety for the distention of the surrounding penis. Illustratively, this predetermined limit is produced by testing the patient before implantation. A tourniquet is applied to the base of the penis and a saline solution is injected into the penis to determine the pressure and volume that is required to satisfy the cosmetic and physical needs of a particular patient. In this way the volume of fluid and the pressure within the reservoir 31 of the device described herein is determined on a patient-by-patient basis.

The pressure relief valve 45 also is a one way flow check valve in which a valve stem 46 is received within a slightly shorter conduit 47. Note also that another conduit 48, angularly oriented relative to the conduit 47 also establishes fluid communication between the reservoir 31 and the expansile section 33. The end of the valve stem 46 that protrudes into the expansile section 33 terminates in a stop 50 that is angularly disposed relative to the conduit 47. This limits the longitudinal depth of travel of the stem through the conduit 47 toward the interior of the storage section 31. Within the fluid storage section 31 the valve stem 46 terminates in a valve seat 51 that, when pressed by fluid pressure within the storage section against the orifices of the conduits 47 and 48, block fluid flow from the storage section 31 into the expansile section 33. When open, however, through a predetermined higher fluid pressure within the expansile section 33, the valve seat 51 is unseated and permits flow from the expansile section into the storage section.

The distal end of the pumping mechanism 30 is connected to a soft but solid extension 52. The extension 52 permits a flaccid dependent penis when the expansile section 33 is not under a charged pressurized state.

The outer surface of the soft, but solid extension 52 forms the inner surface that defines the distal expansile section 33. A flexible membrane 53 is joined on the proximal end to the outer surface of the bladder that forms a fluid storage section 31, the balance of the membrane enclosing the pumping mechanism 30 and the extension 52 to provide the outer elastic surface for the distal expansile section 33.

In operation, an incision is made in the proximal end of the tunica albuginea and the device shown in FIG. 1 is implanted lengthwise on one side of the intercrural septum in one of the two corpora cavernosa. A second device is implanted through another proximal incision in the other corpus cavernosa. In both instances the respective fluid storage sections 31 are surgically lodged in separate ischial cavernosa, under the pubic arch. The expansile sections 33, however, terminate distal to the corona of the glans penis.

In FIG. 1, in order to render one side of a penis rigid, the unique pumping mechanism 30 is pressed between thumb and index finger in order to close the check valve 41 and to express fluid from the interior of the pumping mechanism through the opened check valve 34 and its associated conduit 35 into the distal expansile section 33. Upon releasing the finger pressure, the check valve 34 closes and the relatively lower pressure within the pumping mechanism 30 causes the check valve 41 to open and permit fluid to flow from the storage section 31 into the pumping mechanism 30 by way of the still open conduit 28. To accommodate fluid transferred from the storage section 31 in the foregoing manner, the bellows 40 contracts and the membrane 53 expands to increase the rigidity on one side of the penis. Successive manipulations of the pumping mechanism should bring the side of the penis in question into a satisfactory state of rigidity. Should too much pumping produce an undesirable distention of the penis, the relatively higher fluid pressure in the expansile section 33 will force the pressure relief valve 45 open to permit excess fluid to flow into the fluid storage section 31. In this way, the pressure is relieved in the expansile section 33 and the distention of the penis is reduced to an acceptable level without regard to the number of times the pumping mechanism 30 may be activated.

It will be recalled that a companion to the device shown in FIG. 1 is lodged in the other corpus cavernosa on the other side of the intercrural septum. This parallel, companion device also may be inflated in the manner described above to produce a satisfactory degree of rigidity in the other side of the penis, thereby preparing the penis for satisfactory sexual activity. Upon completion of sexual activity, manual pressure on the penis will increase the fluid pressure in the distal expansile section. This increased pressure will cause the pressure relief valve 45 to open while nevertheless closing the stop 50 and its associated passageway 47. Flow into the reservoir is achieved, however, through the still open conduit 48 and thus permitting the fluid to flow back into the storage section 31, the bellows 40 expanding to compensate for the increased volume of fluid within the storage section 31.

Attention now is invited to FIGS. 2 and 3 which illustrate a conjoined single prosthesis that embodies salient features of the invention. More specifically, a pumping mechanism (not shown in FIGS. 2 and 3) similar to that described in connection with the device shown in FIG. 1 is in fluid communication with fluid storage section 12 that has been pressurized to a level determined in the manner previously described. As the pumping mechanism is successively squeezed between thumb and index fingers as previously mentioned, the pressure in the prosthesis cannot ever exceed a pressure higher than a safe, predetermined level above that which is established in the fluid storage section 12 for the reasons described in connection with the pumping mechanism 30 of FIG. 1. As the limiting pressure is reached the fluid outside of the pumping mechanism will flow back into the fluid storage section 12 during the intervals between each of the successive manipulations of the fingers.

The fluid storage section 12 has two hollow diverging tails 16, 17 that are connected at their common end to the pumping mechanism by means of a flexible expansion and contraction bellows 20. A soft, but solid extension 21 forms one side of a chamber, or distal expansile section 22. The other side of the expansile section 22 is provided by means of a flexible outer membrane 23, this outer membrane covering the entire device, thereby rendering the device one single, integral unit. Thus, as shown, the expansile section 22 is in fluid communication with the pumping mechanism.

In operation and, as best shown in FIG. 3, the thumb and index fingers press in the direction of arrows 24, 25, respectively. This finger pressure expresses fluid within the pumping mechanism into the expansile section 22 in order to inflate the outer membrane 23 causing the penis (not shown) within which the prosthesis is implanted to swell and become rigid. As each charge of fluid is expressed into the expansile section 22, the loss of fluid from the storage section 12 is compensated through contraction of the bellows 20.

To prevent overdistention of the penis, however, as the fluid pressure within the expansile section 22 becomes too high relative to the pressure of the fluid remaining within the pumping mechanism, the higher pressure fluid in the expansile section flows back into the storage section 12. In this manner, an equilibrium is reached between the degree of inflation of the prosthesis and the pressure within the pumping mechanism and the storage section that is commensurate with the rigidity and swelling required for satisfactory sexual activity and a safe distention of the penis.

To restore the penis to a flaccid condition, the penis should be squeezed to press the fluid in the expansile section 22 back into the storage section 12. The bellows 20, during flaccid condition restoration, expands to accommodate the increased volume of fluid entrapped in the storage section 12.

As hereinbefore mentioned, to implant the conjoined single prosthesis within a body, an incision is made in the tunica albuginea (not shown) and the intercrural septum is divided. The prosthesis is then inserted into the penis with the end of the outer membrane 23 and the soft, solid extension 21 that are opposite to the pumping mechanism oriented toward the glans penis. In this circumstance, the prosthesis terminates distal to the corona of the glans penis. As best shown in FIG. 2, the two diverging tails 16, 17 are surgically lodged in separate ischial cavernosa, under the pubic arch.

Attention now is invited to FIG. 4 which shows the distal portion of a prosthetic device that embodies additional features of the invention. The apparatus shown in FIGS. 4, 5 and 6 can be either a single conjoint device or two parallel devices. As shown, four flexible outer membrane 60 enclose portions of a semi-rigid distal storage section which includes a reservoir 70 (FIG. 5) in addition to the storage sections 12 (FIGS. 2, 3) and 31 (FIG. 1) from which an adequate supply of fluid can be drawn to provide a suitably erect and rigid penis.

As shown in FIGS. 4 and 5, a frame 67 encloses the balance of the semi-rigid storage section and gives shape to a reservoir 70 that provides the additional fluid storage volume. The reservoir 70 fuses with the distal outside surface of a pump assembly or pumping mechanism 52A.

Turning now to FIG. 5, as fluid is pumped out of the reservoir 70 and into the four distal expansile cylinders 72,73,74,75 through fluid ports 72A, 73A, 74A, 75A the tunica albuginea 71 becomes, by expansion of chambers 72,73,74 and 75, stretched and expanded and the penis assumes a suitably distended state. As seen in FIG. 4, although the frame 67 is semi rigid, a normal circumferential expansion of the penis of about 3 centimeters is permitted because the four cylinders, when inflated, will give an increased circumference and increased girth to the erect penis.

Illustratively, the outer membranes 60 form four inflatable chambers 72,73,74,75. When inflated for purposes of a satisfactory erection, the penile circumference increases, for example, from 8 cm to 11 cm and the volume of the device increases about 800% to 1000% because the fluid volume increases in the expansile cylinders from 5 cc to 40 or 50 cc. Pressure of the fluid within the cylinders also increases dramatically by as much as 2000%, wherein the fluid pressure increases from 0 to 5 mm Hg to 100 mm of Hg.

It will be recalled that those proximal reservoirs 12 and 31 (FIGS. 1, 2 and 4) in which fluid transfer was compensated for by means of a bellows tended to shrink in an undesirable longitudinal manner when fluid was drawn from the proximal reservoir to produce an erection. Attention is invited to FIG. 4 which shows the bellows 20 enclosed within a rigid frame in the shape of a cylinder 76. The cylinder 76 is joined at the distal end to the pump assembly 52A, and at its proximal end (FIG. 2) to the proximal fluid storage section 12, or (FIG. 1) to the proximal storage section 31.

Thus, as fluid is extracted from the proximal storage sections 12 or 31, the bellows 20 can collapse in a radial direction (80) to accommodate the loss of fluid and yet avoid the longitudinal shrinking that would produce an undesirably shortened erection. As best shown in FIG. 6, fluid is pumped into the distal reservoir 70 through the port 35 in order to inflate the expansile cylinders 72-75. To deflate these cylinders the penis is squeezed and a manifold (not shown) channels flow from apertures 72B, 73B, 74B and 75B into the reservoir 31 (FIG. 4) through a conduit, of which the conduit 77 is typical. The check valve mechanism for establishing fluid communication between the expansile cylinders and the proximal reservoir is identical to that which was described in connection with FIG. 1.

An additional benefit imparted by the cylinder 76 is the more rigid structure that it provides to prevent the buckling and deflection that otherwise might occur in the thrusting that ordinarily accompanies sexual activity. The corrugations on the bellows 20 permit the bellows to draw radially inwardly as illustrated through broken lines 80 in order to compensate for the loss of volume caused by withdrawal of the liquid from the storage sections 12 or 31.

Thus there is provided in accordance with the invention an inexpensive, reliable and relatively easy to implant apparatus for rendering selectively rigid the penis of an otherwise impotent man. Clearly, the cosmetic appearance of this selectively inflatable apparatus is superior to a number of available devices, is less expensive than other inflatable and prosthetic devices, requires less hospitalization and therefore treatment is less expensive for the patient and is expected to provide less chance for a mechanical malfunction. Furthermore, it is expected that the simplicity of implantation will permit its insertion to be performed in the hospital on an ambulatory basis or in the physician's office, under local anesthesia.

I claim:

1. An inflatable prosthetic device for implantation within a penis, said device comprising in combination:
    a semi-rigid fluid storage section and an additional fluid storage section;
    a pumping mechanism integral with and between and in fluid communication through at least one conduit with said fluid storage sections and check valve means in said conduit; and
    flexible membrane means enclosing portions of said semi-rigid section and forming four distal expansile cylinders each in fluid communication through at least one fluid port with said semi-rigid section and thence with said pumping mechanism.

2. An inflatable device according to claim 1 wherein said additional section comprises a bellows in fluid communication with said pumping mechanism, and said device further comprises a rigid frame generally enclosing said bellows and preventing said bellows from shortening the length of said additional section when said fluid is transferred through said bellows to said pumping mechanism.

3. A device according to claim 1 wherein said device is a parallel double prosthesis.

4. A device according to claim 1 wherein said device is a single conjoined prosthesis.

* * * * *